US00PP20780P2

(12) United States Plant Patent
Lambert et al.

(10) Patent No.: US PP20,780 P2
(45) Date of Patent: Feb. 23, 2010

(54) ***HYDRANGEA* PLANT NAMED 'INH-HYD-B4'**

(50) Latin Name: ***Hydrangea* hybrid**
Varietal Denomination: INH-HYD-B4

(76) Inventors: Claudie Lambert, Agrocampus Ouest / INH 2 Rue Andre Le Notre, Angers (FR) 49045; Helene Bertrand, INH 2 Rue Andre Le Notre, Angers (FR) 49045

( * ) Notice: Subject to any disclaimer, the term of this patent is extended or adjusted under 35 U.S.C. 154(b) by 0 days.

(21) Appl. No.: 12/290,497

(22) Filed: Oct. 29, 2008

(51) Int. Cl.
*A01H 5/00* (2006.01)

(52) U.S. Cl. ..... Plt./250

(58) Field of Classification Search ..... Plt./250
See application file for complete search history.

*Primary Examiner*—Annette H Para

(57) ABSTRACT

A new and distinct *Hydrangea* cultivar named 'INH-HYD-B4' is disclosed, characterized by purple/bronze stems and young foliage, and a large inflorescence. The new variety is a *Hydrangea*, suitable for outdoor container and garden purposes.

1 Drawing Sheet

Figure 1:
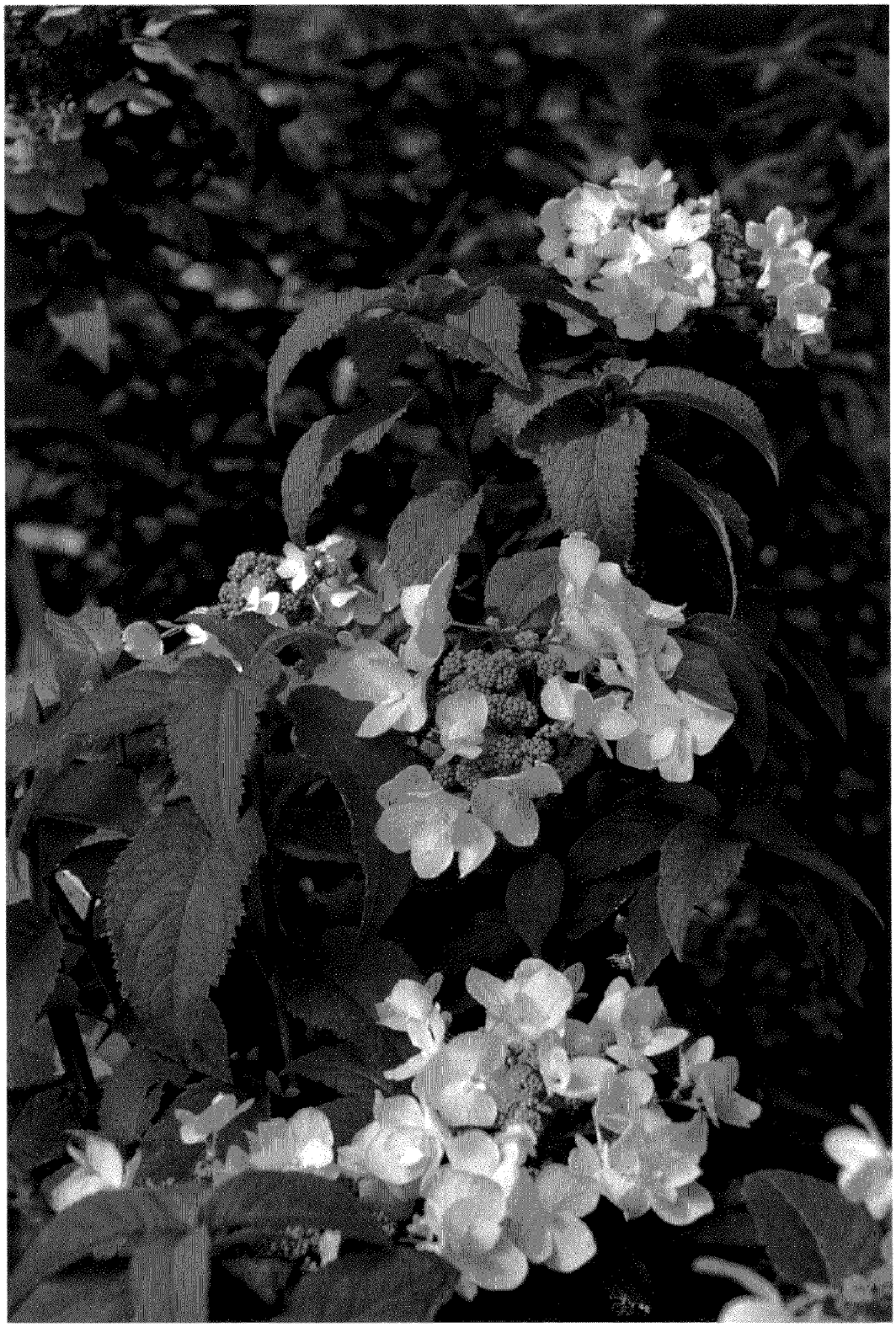

Latin name of the genus and species: *Hydrangea* hybrid. Variety denomination: 'INH-HYD-B4'.

BACKGROUND OF THE INVENTION

The new cultivar is a product of a planned *Hydrangea* breeding program, from the Institut National d'Horticulture located in Angers, France. The new variety was discovered as a seedling from the planned breeding program. This seedling is a result from a crossing made in July 2001 of the female parent, an undistributed proprietary variety referred to as 347 with the male parent, an undistributed proprietary variety referred to as 346. It was selected by Claudie Lambert and Helene Bertrand during the Summer of 2005 in at the research facility in Angers, France.

Asexual reproduction of the new cultivar 'INH-HYD-B4' by vegetative cuttings was first performed in Angers, France at the Institut Nation d'Horticulture, during the Spring of 2006 and has shown that the unique features of this cultivar are stable and reproduced true to type on successive generations.

SUMMARY OF THE INVENTION

The cultivar 'INH-HYD-B4' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'INH-HYD-B4' These characteristics in combination distinguish 'INH-HYD-B4' as a new and distinct *Hydrangea* cultivar:

1. Pubescent leaves with red veins on the underside.
2. Unique coloration of the stems; young stems are red/purple, turning bronze with age.
3. Corymbiform inflorescence with numerous large, sterile flowers.
4. White petals when produced in shady locations, turning pink in full sun.
5. Large sterile flowers with white petaloid sepals and light pink small petals.
6. Sterile, small central flowers.

PARENTAL COMPARISON

Plants of the new cultivar 'INH-HYD-B4' are similar to plants of the female parent, '347,' in most horticultural characteristics, however, plaints of the new cultivar 'INH-HYD-B4' have longer lateral branches, shorter petioles and a larger quantity of flowers. Additionally, plants of the new cultivar are sterile.

'INH-HYD-B4' differs from the male parent '346' in foliage and stem color. Foliage and stems of the new cultivar are much darker than the male parent. Additionally, plants of the new variety have more flowers, and are sterile.

COMMERCIAL COMPARISON

Plants of the new cultivar 'INH-HYD-B4' are similar to plants of the commercial variety *Hydrangea aspera* 'Macrophylla' unpatented in the United States, in many characteristics important to commercial growers. However, plants of the new cultivar 'INH-HYD-B4' differ in foliage and stem color, inflorescence colors has more pink in the new cultivar, and the new cultivar has a larger quantity of flowers.

BRIEF DESCRIPTION OF THE PHOTOGRAPH

The accompanying photograph in FIG. 1 illustrates in full color a typical blooming plant of 'INH-HYD-B4' grown outdoors, in half shade, in Angers, France. Age of the plant in the photograph is approximately 2 years. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'INH-HYD-B4' plants grown outdoors, in full sun, in Angers, France from October 2006 to October 2008. The growing temperature ranged from 10° C. to 17° C. at night to 12° C. to 35° C. during the day. Measurements and numerical values represent averages of typical flowering types.

Botanical classification: *Hydrangea* hybrid cultivar 'INH-HYD-B4.'

PROPAGATION

Time to rooting: 15 to 20 days at approximately 20° C.

Root description: Fine, fibrous, white.

PLANT

Age of the plant described: Approximately 2 years.

Growth habit: Shrub.

Height: Approximately 60 cm.

Plant spread: Approximately 70 cm.

Growth rate: 30 cm/year.

Branching characteristics: Dense, spreading.

Length of lateral branches: Average 25 cm.

Number of lateral branches: Average 32.

Diameter of lateral branches: Approximately 0.4 cm.

Pinching required: No.

Lateral branch shape: Slightly flexible.

Lateral branch strength: Moderate.

Lateral branch color: Near RHS Greyed-Orange 177B with light striping of Greyed-Orange 165B.

Other stem or plant characteristics:

*Lenticel length.*—Approximately 0.1 cm.

*Lenticel width.*—Approximately 0.05 cm.

*Lenticel color.*—About RHS Orange-White 159A.

*Growing stems.*—Red-purple Greyed-Purple 185B.

*Stem pubescence.*—Yes.

Number of leaves per lateral branch: Average 10.

Age of plant described: Approximately 2 years.

FOLIAGE

Leaf:

*Arrangement.*—Opposite.

*Compound or single.*—Single.

*Average length.*—Approximately 10,5 cm.

*Average width.*—Approximately 6 cm.

*Shape of blade.*—Ovate to elliptic.

*Apex.*—Acuminate.

*Base.*—Rounded or attenuate.

*Attachment.*—Opposite.

*Margin.*—Serrate.

*Texture of top surface.*—Rough.

*Texture of bottom surface.*—Rough.

*Leaf internode length.*—Approximately 5 cm.

*Color.*—Young foliage upper side: Near R.H.S. Green 137C. Young foliage under side: Near R.H.S. Green 138C. Mature foliage upper side: Near R.H.S. Green 137A. Mature foliage under side: Near R.H.S. Green 138C.

*Venation.*—Type: pinnate. Venation color upper side: Near R.H.S. primary veins Greyed-Purple 186C, secondary veins Greyed Yellow 160C. Venation color under side: Near R.H.S. Greyed-Purple 185C.

*Durability of foliage to stresses.*—Moderate.

Petiole:

*Average length.*—Approximately 3.3 cm.

*Diameter.*—Approximately 0.25 cm. Color.—Near R.H.S. Greyed-Purple 185B.

FLOWER

Bloom period:

*Natural season.*—July and August.

*Greenhouse production.*—Approximately 4 weeks.

Inflorescence:

*Arrangement.*—Corymbiform.

*Type.*—Hybrid of Mophead and lace cap. Not completely mophead, but with more sterile flowers than lacecap.

*Height.*—Average 10 cm.

*Width.*—Average 19 cm.

*Quantity of flowers per inflorescence.*—Fertile/Complete flowers, approximately 350 Sterile Flowers, approximately 70.

Bud:

*Bud shape.*—Globular.

*Bud length.*—Approximately 0.2 cm.

*Bud diameter.*—Approximately 0.1 cm.

*Bud color.*—Near R.H.S. Red-Purple 69C.

*Base/calyx.*—Near R.H.S. Greyed-Green 193B.

Flower:

*Shape.*—Rotate.

*Facing direction.*—Upright.

*Quantity of flowers per lateral stem.*—About 9 sterile and 50 fertile.

*Quantity of flowers and buds per plant.*—Approximately 15 inflorescences or 6 300 flowers.

*Diameter of entire flower.*—Fertile: Approximately 0.2 cm. Sterile: Approximately 3.5 cm.

*Depth of flower.*—Fertile: Approximately 0.1 cm. Sterile: Approximately 0.1 cm.

*Rate of opening.*—Individual flowers: Fully open approximately 2 days from the bud stage. Whole Plant: Approximately 60% of flowers open at once.

*Flower longevity on plant.*—Fertile flowers: Approximately 2 days. Sterile flowers: Approximately 21 days.

*Persistent or self-cleaning.*—Persistent.

*Fragrance.*—Yes, light.

Petals:

*Length of petal.*—Approximately 0.1 cm.

*Width of petal.*—Approximately 0.05 cm.

*Apex.*—Acute.

*Shape of petal.*—Elliptic.

*Petal margin.*—Entire.

*Petal arrangement.*—One whorl.

*Petal number.*—4 to 5.

*Petals fused.*—No.

*Petal appearance.*—Dull.

*Petal texture.*—Fleshy.

Color: In half shade, flowers are pure white, as shown in the accompanying FIG. 1. Produced in full sun, coloration is as follows:

*Upper surface at first opening.*—Near RHS Purple 75A.

*Upper surface at maturity.*—Near RHS Purple 75A.

*Upper surface at fading.*—Near RHS Fading to pure white.

*Under surface at first opening.*—Near RHS 69C.

*Under surface at maturity.*—Near RHS 75B.

*Under surface at fading.*—Near RHS Fading to pure white.

*Petaloids.*—Petaloid sepals on sterile flowers.

CALYX

| Fertile/Complete flowers | Sterile flowers |
|---|---|
| Present: yes | yes |
| Shape: campanulate | rotate |
| Length: Approximately 0.1 cm. | 1.6 cm |
| Diameter: Approximately 0.1 cm | 3.5 cm |

SEPAL

| Fertile/Complete flowers | Sterile flowers |
|---|---|
| Number: 4 | 4 to 5 |
| Sepal Appearance: glabrous | glabrous |
| Sepal Arrangement: one whorl | one whorl |
| Sepal length: Approximately 0 05 cm. | 1.6 cm |
| Sepal width: Approximately 0.05 cm. | 1.5 cm |
| Sepal shape: triangular | rounded to broad ovate |
| Base: broad | attenuate |
| Apex shape: acute | rounded to acute |
| Margin: entire | entire |
| Color: Near R.H.S. Greyed- Green 193B | white |

PEDUNCLE

Length: Approximately 4 cm.
Diameter: Approximately 0.15 cm.
Angle: 45°.
Strength: Straight.
Color: Near R.H.S. Greyed-Green 193B.

PEDICEL

Present: Yes.
Length: Average 1.5 cm.
Diameter: Approximately 0.1 cm.
Angle: Approximately 45 degrees.
Strength: Straight.
Color: Near RHS Red-Purple 63D.

REPRODUCTIVE ORGANS

*Number of pistils per flower.*—2 to 3.
*Pistil Length.*—Approximately 0.1 cm.
*Stigma shape.*—Fan-shaped.
*Stigma color.*—Near RHS white N155B.
*Style color.*—Near RHS white N155B.
*Style length.*—Approximately 0.05 cm.
*Ovary color.*—Near RHS white N155B.
*Stamens quantity.*—12.
*Anther shape.*—Folded, atrophied.
*Anther size.*—0.05 cm.
*Anther color.*—Near RHS Purple 76A.
*Pollen color.*—No pollen.
*Pollen quantity.*—No pollen.

OTHER CHARACTERISTICS

Fruit/seed production: No fruits produced.

Disease resistance: Neither resistance nor susceptibility to diseases or pests has been observed in this variety.

Drought tolerance and cold tolerance: Semi-hardy perennial, tolerant of some high temperatures. Upper limit of temperature tolerance has not been observed, however, known to tolerate temperatures of at least up to 35° C. Lower limits have also not been observed, however, observed hardy to −10° C. No drought tolerance has been observed.

What is claimed is:

1. A new and distinct cultivar of *Hydrangea* plant named 'INH-HYD-B4' as herein illustrated and described.

* * * * *